(12) United States Patent
Mordau et al.

(10) Patent No.: US 7,573,576 B2
(45) Date of Patent: Aug. 11, 2009

(54) OPTICAL SENSOR DEVICE

(75) Inventors: Ulf Mordau, Reisslingen (DE); Ulrich Backes, Radolfzell (DE)

(73) Assignee: TRW Automotive Electronics Components GmbH & Co. KG, Radolfzell (DE)

( * ) Notice: Subject to any disclaimer, the term of this patent is extended or adjusted under 35 U.S.C. 154(b) by 135 days.

(21) Appl. No.: 11/652,854

(22) Filed: Jan. 12, 2007

(65) Prior Publication Data

US 2007/0165232 A1 Jul. 19, 2007

(30) Foreign Application Priority Data

Jan. 18, 2006 (DE) .................. 20 2006 000 742 U

(51) Int. Cl.
*G01N 21/55* (2006.01)

(52) U.S. Cl. ............. 356/445; 250/227.24; 250/227.25; 356/442; 356/239.8

(58) Field of Classification Search ................. 356/445, 356/442, 239.7, 239.8; 250/227.24, 227.25
See application file for complete search history.

(56) References Cited

U.S. PATENT DOCUMENTS

| | | | | |
|---|---|---|---|---|
| 4,676,638 A | * | 6/1987 | Yasuda | ..................... 356/239.8 |
| 5,661,303 A | | 8/1997 | Teder | |
| 5,898,183 A | * | 4/1999 | Teder | ..................... 250/227.25 |
| 6,018,165 A | | 1/2000 | Kerkmann et al. | |
| 6,064,059 A | | 5/2000 | Pientka et al. | |
| 6,802,631 B1 | | 10/2004 | Hog et al. | |
| 6,842,271 B2 | | 1/2005 | Sautter et al. | |
| 2003/0074962 A1 | | 4/2003 | Sautter et al. | |
| 2006/0006318 A1 | | 1/2006 | Ishikawa et al. | |

FOREIGN PATENT DOCUMENTS

| | | |
|---|---|---|
| DE | 19713909 | 11/1998 |
| DE | 19821335 | 7/2000 |
| DE | 19933642 | 3/2001 |
| DE | 19951831 | 5/2001 |
| DE | 10060964 | 6/2002 |
| DE | 10229200 | 6/2003 |
| EP | 0833764 | 7/2003 |
| WO | 99/47396 | 9/1999 |

\* cited by examiner

*Primary Examiner*—L. G Lauchman
*Assistant Examiner*—Iyabo S Alli
(74) *Attorney, Agent, or Firm*—Tarolli, Sundheim, Covell & Tummino LLP

(57) ABSTRACT

An optical sensor device includes a photoconductor structure having first and second partial members (16, 18) and a coupling surface (20) for coupling the optical sensor device to an opposing counter surface of a pane (22), particularly a windscreen of a motor vehicle. The optical sensor device further includes an optical transmitter (10) coupling a beam of rays into the first partial member (16), an optical receiver (12) receiveing a beam of rays emerging from the second partial member (18), and a printed circuit board (14) arranged parallel to the coupling surface (20). The transmitter (10) and the receiver (12) are arranged on the printed circuit board (14). The photoconductor structure is designed so that the central ray (28) of the transmitter (10) enters into the first partial member (16) perpendicularly to the coupling surface (20) and emerges from the second partial member (18) perpendicularly to the coupling surface (20).

4 Claims, 3 Drawing Sheets

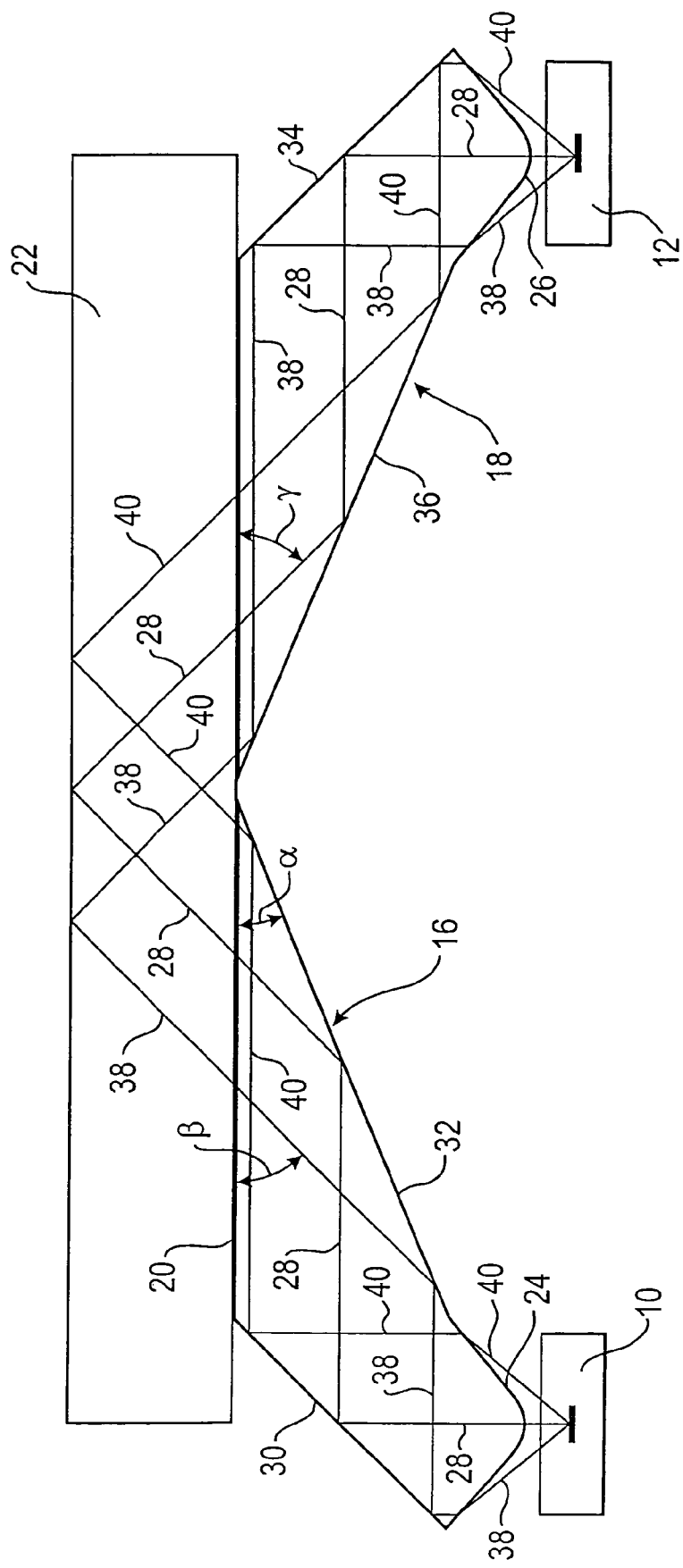

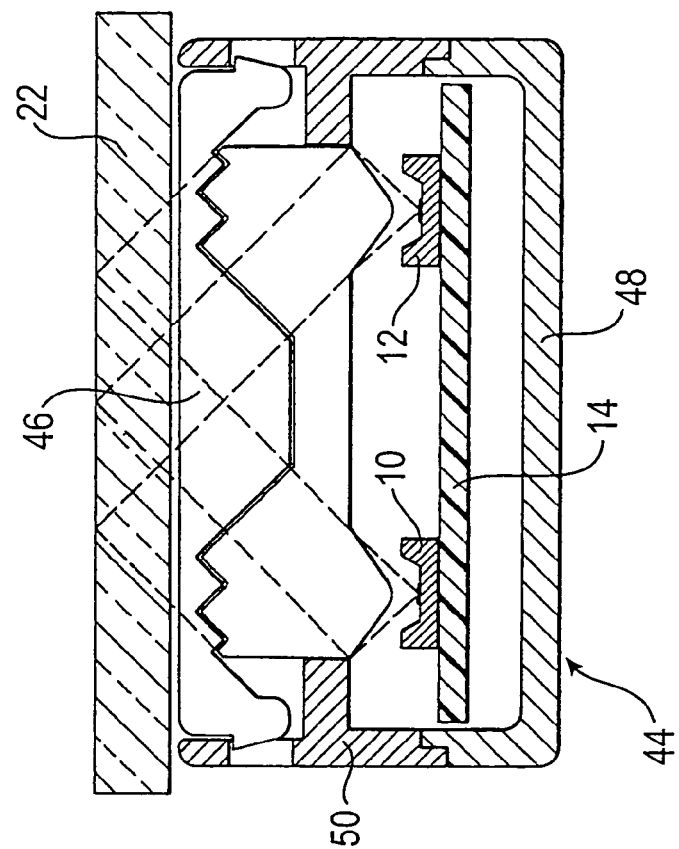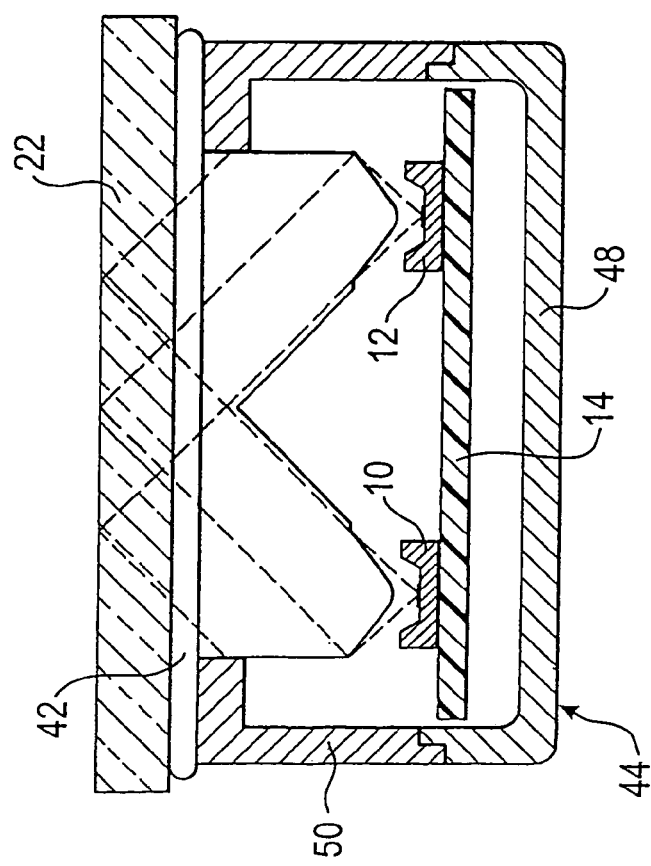

OPTICAL SENSOR DEVICE

TECHNICAL FIELD

The invention relates to an optical sensor device.

BACKGROUND OF THE INVENTION

An optical sensor device comprising a photoconductor structure having first and second partial members and a coupling surface for coupling the optical sensor device to an opposing counter surface of a pane, particularly a windscreen of a motor vehicle, an optical transmitter coupling a beam of rays into the first partial member, an optical receiver receiving a beam of rays emerging from the second partial member, and a printed circuit board on which the transmitter and the receiver are arranged, is known from EP 0 833 764 B1. In this known device, the printed circuit board is arranged perpendicularly to the windscreen of a motor vehicle. The beam of light which is emitted from the transmitter parallel to the plane of the windscreen is coupled into the windscreen via an input section of a radiation conductor. To do this, the beam of light is initially deflected at a first deflection surface through 90 degrees in a direction parallel to the printed circuit board, before it emerges from the input section and enters into the windscreen via two further deflection surfaces through a coupling surface arranged parallel to the windscreen. After several reflections in the windscreen, the beam of light emerges from the windscreen and is directed onto the receiver on the printed circuit board via an output section formed symmetrically to the input section.

It is an object of the invention to provide an optical sensor device with a simpler and more compact construction which is able to be produced at a more favourable cost.

SUMMARY OF THE INVENTION

According to the invention, an optical sensor device comprises a photoconductor structure having first and second partial members and a coupling surface for coupling the optical sensor device to an opposing counter surface of a pane, particularly a windscreen of a motor vehicle. The optical sensor device further comprises an optical transmitter coupling a beam of rays into the first partial member, an optical receiver receiving a beam of rays emerging from the second partial member, and a printed circuit board arranged parallel to the coupling surface. The transmitter and the receiver are arranged on the printed circuit board. The photoconductor structure is designed so that the central ray of the transmitter enters into the first partial member perpendicularly to the coupling surface and emerges from the second partial member perpendicularly to the coupling surface. The arrangement of the printed circuit board with the transmitter and the receiver in accordance with the invention not only saves structural space in the direction perpendicular to the windscreen, but in addition makes possible a construction with fewer deflection surfaces. Compared with the construction known from EP 0 833 764 B1, in which the beam of light emitted from the transmitter is deflected three times before it enters into the windscreen, only two deflection surfaces are necessary in the construction according to the invention. The same applies to the directing of beams to the receiver after emergence from the windscreen.

BRIEF DESCRIPTION OF THE DRAWINGS

FIG. 1 shows an unfolded two-dimensional illustration of the optical components of a sensor device according to the invention;

FIGS. 2a, 2b show sectional views of the sensor device according to the invention with different kinds of coupling to a pane; and FIG. 3 shows an exploded view of the sensor device of FIG. 2a.

DETAILED DESCRIPTION OF THE PREFERRED EMBODIMENT

Figure 3:
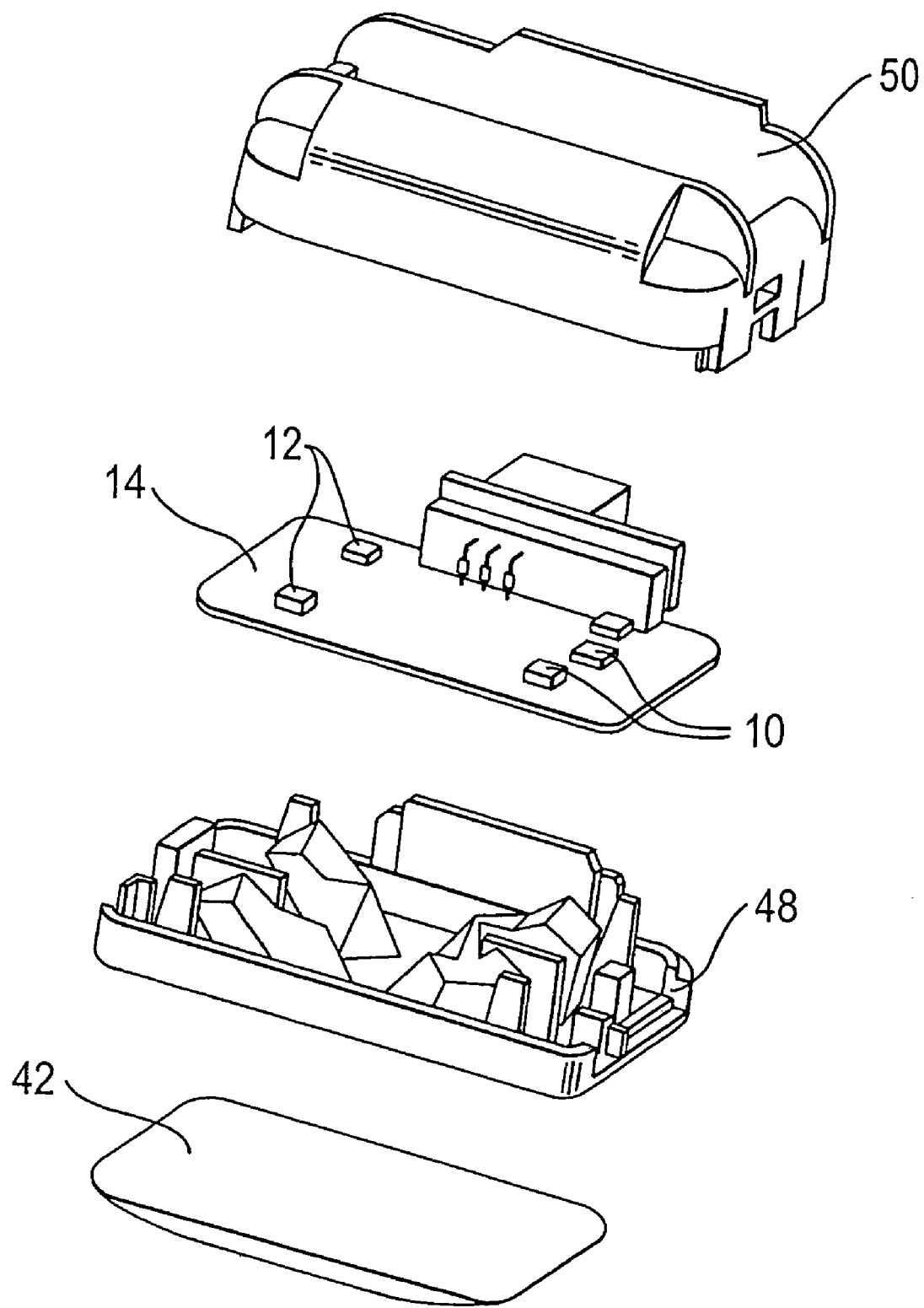

An unfolded two-dimensional illustration of the optical components of a sensor device is shown in FIG. 1, i.e. FIG. 1 is not a conventional sectional view. The unfolded illustration was selected because the basic structure of the sensor device and the path of rays can be seen better therein than in a sectional illustration. In addition, the actual three-dimensional form of the sensor device is not essential for the invention.

The sensor device has an optical transmitter 10 and an optical receiver 12 in the form of an infrared transmission diode and an infrared reception diode respectively, which are arranged on a printed circuit board 14 (not illustrated in FIG. 1). A photoconductor structure is basically made up of two identically constructed partial members 16, 18 which together form a symmetrical continuous photoconductor body made of transparent plastic material. The photoconductor structure is coupled with a coupling surface 20 to an opposing counter surface of a pane 22. The contact surface 20 is arranged parallel to the printed circuit board 14 carrying the transmitter 10 and the receiver 12, so that the printed circuit board 14 likewise extends in a plane parallel to the pane 22. An aspherical lens 24 is formed on the end of the first partial member 16 facing the transmitter 10, i.e. the said lens faces the transmitter 10. A second aspherical lens 26 is formed on the second partial member 18 and faces the receiver 12.

A beam of light emitted from the transmitter 10 enters into the first partial member 16 of the photoconductor structure through the first aspherical lens 24. Of this beam only the central ray 28, which enters into the first partial member 16 in a direction perpendicular to the coupling surface 20, will be discussed at this time. The central ray 28 is deflected under total reflection through 90 degrees at a first deflection surface 30 which is inclined at a 45 degree angle to the central ray 28, so that the said ray is oriented parallel to the coupling surface 20. After a further total reflection at a second deflection surface 32 which faces the first deflection surface 30 and is inclined at a specific acute angle α to the coupling surface 20, the central ray 28 emerges from the first partial member 16 through the coupling surface 20 and enters into the pane 22 under a defined entry angle β.

The central ray 28 undergoes a single total reflection on the inner surface of the pane 22 opposite the coupling surface 20, and emerges from the pane 22 at an exit angle γ, which corresponds to the entry angle β, and arrives through the coupling surface 20 into the second partial member 18 of the photoconductor structure. Owing to the symmetrical construction of the photoconductor structure, the path of rays in the second partial member 18 is symmetrical to the path of rays in the first partial member 16, i.e. the central ray 28 is oriented parallel to the coupling surface 20 after a first total reflection on a third deflection surface 34, and is oriented perpendicularly to the coupling surface 20 after a second total reflection on a fourth deflection surface 36. The central ray 28 therefore emerges from the second partial member 18 perpendicularly to the coupling surface 20 through the second aspherical lens 26 and strikes onto the receiver 12 which is arranged on the printed circuit board 14.

In FIG. 1 also the path of rays of two peripheral rays 38, 40 of the light beam is illustrated. The first aspherical lens 24 ensures that all the rays of the light beam enter into the first partial member 16 parallel to the central ray 28. In the photoconductor structure and in the pane 22, all the rays undergo the same five total reflections (two in the first partial member 16, one in the pane 22 and two in the second partial member 18), like the central ray 28. The second aspherical lens 26 on the second partial member 8 bundles together the light rays emerging from the photoconductor structure, so that all the rays are directed to the receiver 12.

In FIGS. 2a and 2b two variants of the coupling of the sensor device to the pane 22 are shown. According to the variant of FIG. 2a, an elastic cushion 42 is provided between the sensor device and the pane 22, whereas in the variant of FIG. 2b a structure coupler 46, which is fastened to the housing 44 of the sensor device, is glued onto the pane 22.

FIG. 3 shows the individual parts of the sensor device of FIG. 2a. The printed circuit board 14 and two sets of the optical components described above are accommodated in the housing 44, which includes a housing part 48 facing the elastic cushion 42 and the pane 22, and a cover 50. According to the two sets of optical components, two transmitters 20 and two receives 12 are arranged on the printed circuit board 14.

The optical sensor device is particularly suitable, but not exclusively, as a rain sensor which can be arranged on the windscreen of a motor vehicle.

The invention claimed is:

1. A sensor for use in sensing the presence of moisture on an outer side surface of a windshield of a vehicle, said sensor comprising:

an optical transmitter having a source of light rays which is energizable to provide an array of light rays, an optical receiver which receives an array of light rays reflected from the outer side surface of the windshield, and a photoconductor structure which receives the array of light rays from said optical transmitter, directs light rays from said optical transmitter toward an inner side surface of the windshield, receives light rays reflected from the outer side surface of the windshield, and directs light rays reflected from the outer side surface of the windshield to said optical receiver, said photoconductor having a first aspherical lens disposed adjacent to said optical transmitter with a central axis of an curving surface of said first aspeherical lens coincident with a central axis of said source of light rays of said optical transmitter, said first aspherical lens being effective to receive peripheral rays of light exiting from said source of light rays along paths which diverge in opposite directions from the central axis of said source of light rays and to receive a ray of light exiting from said source of light rays along a path which is coincident with the central axis of said source of light rays, said curving surface of said first aspherical lens being convex in a direction toward said optical transmitter, said photoconductor having a second aspherical lens disposed adjacent to said optical receiver with a central axis of an curving surface of said second aspherical lens coincident with a central axis of said optical receiver, said second aspherical lens being effective to direct peripheral rays of light exiting from said second aspherical lens along paths which converge in opposite directions toward the central axis of said optical receiver and to direct a ray of light exiting from said second asymmetrical lens along a path which is coincident with the central axis of said optical receiver, said arcuately curving surface of said second aspherical lens being convex in a direction toward said optical receiver.

2. A sensor as set forth in claim 1 said first aspherical lens is effective to deflect said peripheral rays of light exiting from said source of light to paths which extend parallel to the central axis of said curving surface of said first aspherical lens, said second aspherical lens is effective to deflect rays of light transmitted along paths extending parallel to the central axis of said curving surface of said second aspherical lens to paths extending transverse to the central axis of said curving surface of said second aspherical lens.

3. A sensor as set forth in claim 1 further including an elastic cushion disposed between said photoconductor and the inner side surface of the windshield.

4. A sensor as set forth in claim 1 further including a structure coupler through which rays of light are directed from said photoconductor structure toward the inner side surface of the windshield, said structure coupler being effective to receive rays of light reflected from the outer side surface of the windshield and to direct rays of light to said photo conductor structure.

\* \* \* \* \*